US007241797B2

(12) United States Patent
Horseman

(10) Patent No.: US 7,241,797 B2
(45) Date of Patent: Jul. 10, 2007

(54) METHOD OF INCREASING MILK PRODUCTION

(75) Inventor: Nelson D. Horseman, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 364 days.

(21) Appl. No.: 10/351,474

(22) Filed: Jan. 22, 2003

(65) Prior Publication Data
US 2003/0139420 A1 Jul. 24, 2003

Related U.S. Application Data

(60) Provisional application No. 60/351,134, filed on Jan. 23, 2002.

(51) Int. Cl.
*A61K 31/4045* (2006.01)
(52) U.S. Cl. .................... 514/412; 514/565; 514/567; 514/615
(58) Field of Classification Search ................ 424/451, 424/464, 484, 438; 514/567, 559, 590
See application file for complete search history.

(56) References Cited

U.S. PATENT DOCUMENTS 5,922,341 A 7/1999 Smith et al.
6,331,536 B1 12/2001 Radulovacki et al.

OTHER PUBLICATIONS

Petraglllia et al, Gynecol. obstet. Invest. 23: 103-109, 1987 Prolactin Changes-.*
Muller etal, Prolactin -lowering and -releasing drugs.Mechanism of actin and therapeutic aplications Drugs 25/4 pp. 399-432, 1983□□□□abstract-EMBASE # 83123075.*
Thulin et al. Levodopa in human breast milk; NEUROLOG 50 pp. 1920,1921 Jun. 1998.*
Ben-Jonathan, N. in *Prolactin* (ed. Horseman, N.D.) 1-24 (Kluwer Academic Publishers, Boston, 2001).
Blatchford, D.R., Hendry, K.A., Turner, M.D. Burgoyne, R.D. & Wilde, C.J., "Vectorial secretion by constitutive and regulated secretary pathways in mammary epithelial cells," *Epithelial Cell Biol*, 4, 8-16 (1995).
Briskin, C., et al., "Prolactin controls mammary gland development via direct and indirect mechanisms," *Dev Biol* 210, 96-106 (1999).
Chapman, R.S., et al., "Suppression of epithelial apoptosis and delayed mammary gland involution in mice with a conditional knockout of Stat3," *Genes Dev* 13, 2604-2616 (1999).

(Continued)

*Primary Examiner*—Neil S. Levy
(74) *Attorney, Agent, or Firm*—Frost Brown Todd LLC

(57) ABSTRACT

The invention relates generally to the use of pharmaceutical compositions to increase milk production alone or in combination with certain biological active ingredients. Specifically, the method relates to the use of pharmaceutical compositions that will act on the feedback of the intrinsic regulatory pathway in the mammalian mammary gland. The present invention provides for as a method of increasing bovine milk production as well as a method of correcting certain human lactation abnormalities. Preferably, the compounds used in the methods of the present invention are one or more active agents capable of inhibiting peripheral aromatic amino acid decarboxylase (AADC) enzymes, peripheral tryptophan hydroxylase (TPH) enzymes, peripheral serotonin (5-HT) enzymes, or a combination of enzymes thereof.

22 Claims, 5 Drawing Sheets

OTHER PUBLICATIONS

Diatchenko, L. et al., "Suppression subtractive hybridization: a method for generating differentially regulated or tissue-specific cDNA probes and libraries," *Proc Natl Acad Sci USA*, 93,6025-6030 (1996).

Hardman, J.G. and Limbird, L.E. (eds.) *Goodman & Gillman's The pharmacological basis of therapeutics* (McGraw-Hill, New York, 1996).

Horseman, N. D. et al., "Defective mammopoiesis, but normal hematopoiesis, in mice with a targeted disruption of the prolactin gene," *EMBO J* 16, 6926-6935 (1997).

Hou, M., et al., "Glycosylation-dependent cell adhesion molecule 1 (GlyCAM 1) is induced by prolactin and suppressed by progesterone in mammary epithelium," *Endocrinology* 141, 4278-4283 (2000).

Jerry, D.J., et al., "Delayed involution of the mammary epithelium in BALB/c-p53null mice," *Oncogene* 17, 2305-2312 (1998).

Kang, J. J. et al., "Transcript quantitation in total yeast cellular RNA using kinetic PCR," *Nucleic Acids Res* 28, e2. (2000).

Li, M., et al., "Mammary-deprived signals activate programmed cell death during the first stage of mammary gland involution," *Proc Natl Acad Sci USA* 94, 3425-3430 (1997).

Nguyen, A.V. and Pollard, J.W., "Transforming growth factor beta3 induces cell death during the first stage of mammary gland involution," *Development* 127, 3107-3118 (2000).

Pedchenko, V. K. and Imagawa, W.T., "Mammogenic hormones differentially modulate keratinocyte growth fact (KGF)-induced proliferation and KGF receptor expression in cultured mouse mammary gland epithelium," *Endocrinology* 139, 2519-2526 (1998).

Stoll, J. & Goldman, D., "Isolation and structural characterization of the murine tryptophan hydroxylase gene," *J. Neurosci Res* 28, 457-465 (1991).

Vomachka, A.J., Pratt, S.L., Lockefeer, J.A. and Horseman, N.D., "Prolactin gene-disruption arrests mammary gland development and retards T-antigen-induced tumor growth," *Oncognen* 19, 1077-1084 (2000).

Wilde, C.J., Addey, C.V., Boddy, L.M. and Peaker, M., "Autocrine regulation of milk secretion by a protein in milk," *Biochem J* 305, 51-58 (1995).

Wilde, C.J., Knight, C.H. & Flint, D.J. "Control of milk secretion and apoptosis during mammary involution," *J Mammary Gland Biol Neoplasia*, 4, 129-136. (1999).

Ayalon, Daniel, et al.; "Effect of L-Dopa on Galactopoiesis and Gonadotropin Levels in the Inappropriate Lacation Syndrome"; Journal of Obstetrics of Gynecology; Aug. 1974; pp. 159-170; vol. 44; No. 2; The American College of Obstetricians and Gynecologists.

Malarkey, William B.; "Nonpuerperal Lacation and Normal Prolactic Regulation"; JCE & M; 1975; pp. 198-204; vol. 40; No. 2; Department of Medicine, Division of Endocrinology; The Ohio State University Hospitals, Columbus, Ohio 43210.

Slatopolsky, Cantis, M., et al.; Efecto comparativo de Distintas Drogas en la Inhibicion de la Lacatancia ("In the Inhibition of the Lactation"); Spanish article with English translation; Rev. Esp. Obst. y Gin.; 1985; vol 44; pp. 447-456.

"Tablets Sinemet® (Carbidopa-Levodopa)"; Merck & Co., Inc.; Aug. 2002; pp. 1-12; Whitehouse Station, New Jersey 08889, USA.

Holmes, A., et al., "Abnormal behavioral phenotypes of serotonin transporter knockout mice: Parallels with human anxiety and depression", Biological Psychiatry, Nov. 15, 2003, pp. 953-959, vol. 54, No. 10.

Leman, S., et al., "Density and affinity of 5-HT transporter in a mouse model of depression", Behavioural Pharmacology, Sep. 2005, p. S44, vol. 16, No. Suppl. 1.

Matsuda, M., et al., "Serotonin Regulates Mammary Gland Development via an Autocrine-Paracine Loop", Developmental Cell, Feb. 2004, pp. 193-203, vol. 6, Cell Press.

McManaman J.L., et al., "Mammary physiology and milk secretion", Advanced Drug Delivery Reviews, Apr. 29, 2003, pp. 629-641, vol. 55, No. 5, Elsevier.

Nevile, M.C., et al., "LACTOGENESIS. The Transition from Pregnancy to Lactation", Pediatric Clinics of North America, Feb. 2001, pp. 35-52, vol. 48, No. 1.

Plaut, K., et al., "Effect of Exogenous Prolactic Administration on Lactational Performance of Dairy Cows", Domestic Animal Endocrinology, 1987, pp. 279-290, vol. 4, No. 4, Domendo, Inc.

Ramboz, S., et al., "Serotonin receptor 1A knockout: An animal model of anxiety-related disorder", Proceedings of the National Academy of Sciences of the United States of America, 1998, pp. 11476-14481, vol. 95, No. 24.

Searce-Levie, K., et al., "5-HT receptor knockout mice: Parmacological tools or models of psychiatric disorders. Monogoraph Title: Annals of the New York Academy of Sciences; Molecular and functional diversity of ion channels and receptors", Annals of the New York Academy of Sciences, Apr. 30, 1999, pp. 701-715, vol. 868, New York Academy of Sciences, New York, USA.

Stiening, C.M., et al., "Effect of Lactogenic Stimuli and Serotonin on Secretory Activation of Bovine Mammary Epithelial Cells (BMEC)", The FASEB Journal, The New Biology: Reports, Reviews and FJ Express, Experimental Biology 2006®, Apr. 1-5, 2006, Abstracts Part I, Abstracts 7.1—485.10, Mar. 6, 2006, vol. 20, No. 4, San Francisco, California.

Vonderhaar, B.K., et al., "The mammary gland. A model for hormonal control of differentiation and preneoplasia", Biological Responses in Cancer, 1985, pp. 125-159, vol. 4, Plenum Press, New York, USA.

Yancey, Jr., R.J., et al., "Efficacy of lincosaminide antibiotics in the treatment of experimental staphyloccoal mastitis in lactating mice", Journal of Antimicrobial Chemotherapy, 1985 (Copyright 1999 Elsevier Science B.V., Amsterdam), United Kingdom.

\* cited by examiner

METHOD OF INCREASING MILK PRODUCTION

This application claims the benefit of U.S. Provisional Patent Application Ser. No. 60/351,134, filed Jan. 23, 2002, which application is hereby incorporated by reference in its entirety.

This invention was made in part with Government support under Grant No. RO1 DK52134 NDH, awarded by the National Institutes of Health. The Government may have certain rights in this invention.

FIELD OF THE INVENTION

The invention relates generally to the use of pharmaceutical compositions to increase milk production alone or in combination with certain biological active ingredients. Specifically, the method relates to the use of pharmaceutical compositions that will act on the feedback of the intrinsic regulatory pathway in the mammalian mammary gland. The present invention provides for as a method of increasing milk production as well as a method of correcting certain mammalian lactation abnormalities.

BACKGROUND OF THE INVENTION

Basically, lactation is regulated by a dynamic balance between endocrine stimulation and feedback inhibition from local "milk stasis" signals (Wilde, C. J., Knight, C. H. & Flint, D. J. Control of milk secretion and apoptosis during mammary involution. *J. Mammary Gland Biol Neoplasia* 4, 129-136. (1999)). Milk stasis feedback may contribute to lactational insufficiency in women, and is an important limiting factor in the production of milk in dairy animals. Various serotonin receptor genes are expressed in mammary cells, and therefore the components of an autocrine/paracrine serotonin network are present in the mammary gland. The present invention provides for a method that disrupts serotonin synthesis and signaling causing elevated milk protein gene expression and milk yield. Therefore, the present invention provides for methods for manipulating milk production in women, and in non-human animals.

Serotonin, or 3-(β-aminoethyl)-5-hydroxyindole (5-hydroxytryptophan, or "5-HT") is a neurotransmitter in the central nervous system which is known to play an important role in the pathogenesis of affective illness. Serotonin acts through specific cellular receptors that comprise at least 15 individual subtypes. These receptors can be grouped into at least four families based on structural and functional characteristics. The 5-HT1, 5-HT2 and 5-HT4 families are G-protein coupled receptors linked to enzymatic and electrical effector systems, while the 5-HT3 receptor is a gated ion channel.

The biosynthesis of 5-HT in the brain proceeds from the uptake of dietary tryptophan by the neuron, followed by its conversion to 5-hydroxytryptophan (abbreviated 5-HTP) by an enzyme called tryptophan hydroxlyase. 5-HTP is decarboxylated to 5-HT by an enzyme called L-aromatic amino acid decarboxylase (AADC). When administered to animals or humans, 5-HTP is rapidly decarboxylated by an enzyme called L-amino acid decarboxylase also commonly called peripheral decarboxylase. Carbidopa is an inhibitor of L-aromatic amino acid decarboxylase. Carbidopa does not enter the brain, and thus administration of carbidopa selectively blocks the conversion of 5-HTP to 5-HT in the periphery, but not the brain.

It has now been discovered that administration of various serotonin agonists and antagonists is effective in increasing milk production as well as a method of correcting certain mammalian lactation abnormalities.

Accordingly, in a preferred embodiment, the present invention is directed to the administration of active agents capable of inhibiting peripheral aromatic amino acid decarboxylase (AADC) enzymes, peripheral tryptophan hydroxylase (TPH) enzymes, peripheral serotonin (5-HT) enzymes, or a combination thereof for increasing milk production as well as for correcting certain mammalian lactation abnormalities.

SUMMARY OF THE INVENTION

The invention is based, in part, upon the discovery that the inhibition of the synthesis and/or reception of serotonin during lactation produces an increase in milk production. An active agent that either inhibits serotonin synthesis or inhibits serotonin receptors in the mammary glands may be used to increase milk protein gene expression and milk secretion.

Accordingly, it is a primary object of the invention to address the above-described need in the art by providing a novel method for increasing lactation in a mammal by administering an effective amount of an active agent to a mammal in need of such therapy wherein the active agent is capable of inhibiting peripheral aromatic amino acid decarboxylase (AADC) enzymes, peripheral tryptophan hydroxylase (TPH) enzymes, peripheral serotonin (5-HT) enzymes, or a combination thereof.

It is another object of the invention to provide such a method wherein the pharmacologically active agent is administered orally. It is a further object of the invention to provide such a method wherein the pharmacologically active agent is administered parenterally. It is also an object of the invention to provide such a method wherein the pharmacologically active agent is administered nasally.

It is another object of the invention to provide a method for treating lactation disorders in a mammal by administering an effective amount of a pharmacologically active agent to an individual in need of such therapy, wherein the active agent is a one or more agents selected from the group consisting of peripherally-acting aromatic amino acid decarboxylase (AADC) inhibitors, peripherally-acting tryptophan hydroxylase (TPH) inhibitors, peripherally-acting serotonin (5-HT) receptor antagonists, and mixtures thereof.

It is yet a further object of the invention to provide pharmaceutical formulations for carrying out the aforementioned methods.

Additional objects, advantages and novel features of the invention will be set forth in part in the description which follows, and in part will become apparent to those skilled in the art upon examination of the following, or may be learned by practice of the invention.

In a first aspect of the invention, a method is provided for increasing milk production by a mammal, the method comprising administering to a mammal a pharmaceutical formulation containing one or more agents selected from the group consisting of peripherally-acting aromatic amino acid decarboxylase (AADC) inhibitors, peripherally-acting tryptophan hydroxylase (TPH) inhibitors, peripherally-acting serotonin (5-HT) receptor antagonists, and mixtures thereof.

Administration of the pharmaceutical formulation is carried out within the context of a predetermined dosing regimen such that the agent is effective in the treatment of increasing lactation. Drug delivery may be accomplished through any route effective to provide increased lactation, including oral, parenteral, buccal, rectal, topical, and transdermal.

DETAILED DESCRIPTION OF THE INVENTION

Figure 1:
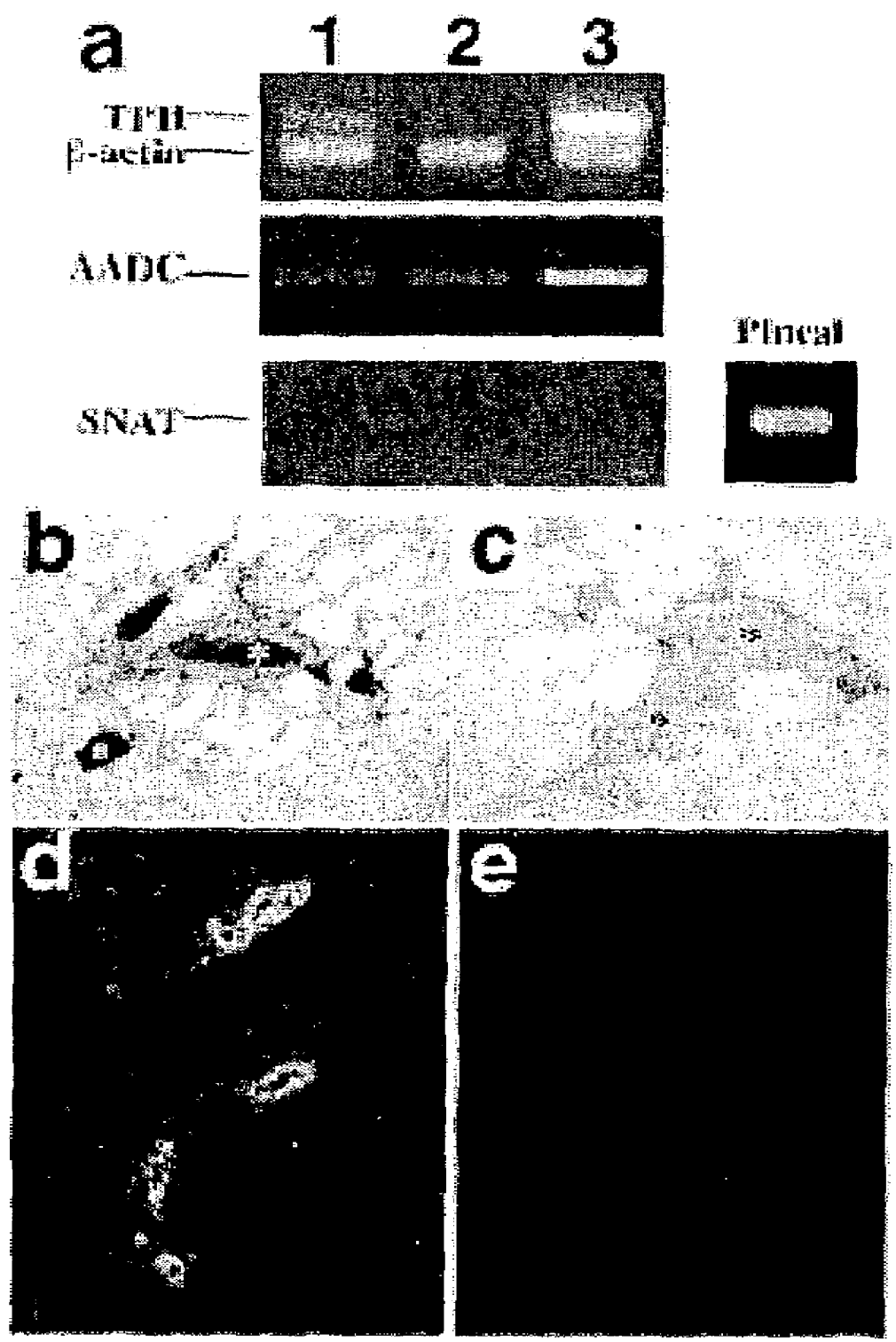
FIG. 1 shows TPH expression and 5-HT synthesis in mouse mammary glands. (a) Expression of mRNA for indoleamine-synthesizing enzymes was examined by RT-PCR. Messenger RNAs for the two enzymes necessary for 5-HT synthesis (TPH and AADC) were expressed in the mammary gland. Serotonin N-acetyl transferase mRNA (SNAT), which is necessary for melatonin synthesis, was not detectable in mammary gland, but was detected in the positive control (pineal). Lane 1: sham operated control, lane 2: progesterone treated, lane 3: pituitary grafted. (b and c) In-situ hybridization analysis with the digoxygenin-labeled cRNA probes for TPH in a pituitary graft-stimulated (b) and unstimulated (c) mammary gland. Antisense probe-specific signal (*) was observed in each epithelial cell in mammary glands. In situ hybridization was performed following a protocol for DIG RNA Labeling system (Boeringer Ingleheim GmbH, Ingelheim, Germany). Five-µm paraformaldehyde-fixed paraffin sections were hybridized with digoxygenin-labeled sense (negative control, not shown) or antisense cRNA probe corresponding to 5' end of TPH mRNA (approx. 200 bases). (d and e) Paraffin sections of mouse mammary tissue taken on day 18 after pituitary grafting were immunostained with monoclonal anti-5-HT (panel b) or control IgG (panel c). Accumulation of 5-HT (lucent signal) was detected in the mammary gland epithelium.

The invention provides methods for regulating the feedback of the intrinsic regulatory pathway in the mammalian mammary gland. The present invention can be applied as a method of increasing milk production or as a method of correcting certain lactation abnormalities or lactation failure in a mammal.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a combination of two or more pharmacologically active agents, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacological effect. Included are derivatives and analogs of those compounds or classes of compounds specifically mentioned which also induce the desired pharmacological effect.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

The term "treat" or "treating" as used herein includes therapeutic and prophylaxis of the symptoms and named condition and amelioration or elimination of the conditions once it has been established.

The terms "enhancing" or "increasing", when used herein in reference to lactation, is defined as promoting the initiation, increase, or other enhancement to lactation including, without limitation, increasing the rate at which milk production or secretion occurs within the mammary tissues, increasing the total volume of milk produced or secreted by a mammal or aiding in the prevention of lactation disorders or other lactation-related defects. The term also refers to any enhancement or other augmentation of mammary gland function.

As used here and, the term "lactation" means the production of milk and/or or secretion of milk by the mammary glands of a mammal or the period following giving birth during which milk is secreted in the breasts of a mammal. By "lactation failure" or "lactation abnormalities" is meant both when the female mammal has no milk production or secretion or when an insufficient amount of milk production and secretion or is at special risk for such a state. The invention also relates to a prophylactic treatment of expectant mothers who are at special risk for lactation failure.

As used herein, the term "mammal" means the Mammalia class of higher vertebrates. The term "mammal" includes, but is not limited to, a human. In one embodiment, the mammal is a ruminant animal.

As used herein, the term "ruminant" means an even-toed hoofed animal that has a complex 3-chamber or 4-chamber stomach and which typically re-chews what it has previously swallowed. Some non-exhaustive examples of ruminants include cattle, sheep, goats, oxen, muskox, llamas, alpacas, guanicos, deer, bison, antelopes, camels, and giraffes. Preferably, the mammals are of ovine, caprine, bovine or porcine species. More preferably, the mammal is a bovine species.

In one embodiment, the present invention provides a method of enhancing lactation or treating a lactation disorder in an a mammal comprising administering to the mammal a pharmaceutical formulation containing a pharmacologically active agent of a type and in an amount effective to increase lactation, including the production and/or secretion of milk by the mammal.

In another embodiment, the present invention provides a method of initiating, increasing, or enhancing lactation in an a mammal comprising administering to the mammal a pharmaceutical formulation containing a pharmacologically active agent of a type and in an amount effective to potentiate the action of a serotonin in the mammary glands.

In another embodiment, the present invention provides a method of initiating, increasing, or enhancing lactation in an a mammal comprising administering to the mammal a pharmaceutical formulation containing a pharmacologically active agent of a type and in an amount effective to inhibit the action of a serotonin in the mammary glands.

As used herein, the term "inhibit the action of a serotonin" or "inhibition of serotonin action" in the mammary glands refers to an inhibition or decrease in the serotonin synthesis in the mammary glands or an inhibition or decrease in the reception of serotonin by receptors or action of serotonin receptors or receptor pathway in the mammary glands. An active agent that either inhibits serotonin synthesis or inhibits serotonin receptors in the mammary glands may be used for initiating, increasing, or enhancing lactation, including milk protein gene expression and/or milk secretion.

Specifically, the invention provides for the use of a compound that either inhibits 5HT synthesis or blocks the 5HT receptors in the mammary glands in order to regulate lactation and milk production. More specifically, the method of treatment is by the use of any compound that sufficiently inhibits the action of serotonin within the mammary glands with a compound or compounds that act in the peripheral system and not within the central nervous system. More specifically, the treatment is by one or more compounds selected from the group consisting of peripherally-acting aromatic amino acid decarboxylase (AADC) inhibitors, peripherally-acting tryptophan hydroxylase (TPH) inhibitors, peripherally-acting serotonin (5-HT) receptor antagonists, and mixtures thereof. As used herein, the term "peripherally-acting" means the method of treatment must be by a compound which either (a) substantially does not cross the blood-brain barrier or (b) substantially acts in the peripheral system and not within the central nervous system.

The invention also relates to a method for the treatment of lactation failure or abnormality in a mammal, comprising administering to the mammal a pharmaceutical formulation containing a pharmacologically active agent of a type and in an amount effective to increase lactation or the production and secretion of milk by the mammal. This administration could be subcutaneous, intramuscular, intravenous, nasal or dermal, preferably subcutaneous.

In another embodiment, the present invention provides for a method for increasing milk production in female mammals used in milk production, including humans, according to which the female mammal is supplied, over a period of the order of 10 to 20 days, on completion of two-thirds of the gestation period, with a pharmaceutical formulation containing a pharmacologically active agent of a type and in an amount effective to increase lactation or the production and secretion of milk by the mammal. Preferably, the treatment is by one or more agents selected from the group consisting of peripherally-acting aromatic amino acid decarboxylase (AADC) inhibitors, peripherally-acting tryptophan hydroxylase (TPH) inhibitors, peripherally-acting serotonin (5-HT) receptor antagonists, and mixtures thereof. In one embodiment, the agent is administered in an amount between about 1 and about 200 milligrams per day, more preferably between about 5 and about 75 milligrams per day.

The invention also relates to a composition comprising one or more agents that sufficiently inhibits the action of serotonin within the mammary glands wherein the agent or agents act in the peripheral system and not within the central nervous system in conjunction with lactational enhancers, together with pharmaceutically acceptable carriers for the treatment of human lactation failure.

The lactational enhancers could be chosen among 11,17-dimethoxy-18-((3,4,5-trimethoxybenzoyl)oxy)yohimban-16-carboxylic acid methyl ester, 4-amino-5-chloro-N-((2-diethylamino)ethyl)-2-methoxybenzamide, somatotropins, cholines, or estrogens.

The lactation can be promoted in the following situations: (i) To normalize lactation volumes in women with lactational failure; (ii) To maintain/enhance lactation in mothers of premature babies who are being cared for in a neonatal unit; (iii) To enhance lactational performance in mothers with twins and triplets; (iv) To promote and prolong lactation in mothers of babies with risk of developing lactose intolerance or other milk allergies if formula milk was used; (v) To enhance lactation in women where suckling frequency is diminished during part of the day, e.g. working mothers; and (vi) To treat mothers prophylactically prior partus with a special risk for having an insufficient amount of milk production.

In order to carry out the method of the invention, a selected pharmacologically active agent is administered to a mammal in need of such treatment. In a first embodiment, the active agent may be administered orally, parenterally, buccally, rectally, or transdermally.

Inhibitors of enzymes involved in 5HT synthesis include irreversible tryptophan hydroxylase inhibitors (DL-parachlorophenylalanine, 6-Flurotryptophan and L-propyldoracetamide) and inhibitors of 5HTP decarboxylase (carbidopa and 1-methyl-5HTP).

In one embodiment, the serotonin receptor antagonist is selected from the group consisting of ketanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, granisetron, LSD, 2-bromo-CSD (BOL), xylamidine, and 1-(−)-cocaine. In the preferred embodiment, active agents are exerted only in the peripheral nervous system. In one embodiment, the peripheral serotonin receptor antagonist is administered in an amount of at least about 0.01 mg per 100 kg body weight, preferably at least about 0.1 mg per 100 kg body weight, and more preferably at least about 1 mg per 100 kg body weight. The peripheral serotonin receptor antagonist is generally administered in an amount of at most about 500 mg per 100 kg body weight, preferably at most about 250 mg per 100 kg body weight, and more preferably at most about 100 mg per 100 kg body weight.

In another embodiment, the active agent is an inhibitor of aromatic L-amino acid decarboxylase (AADC). Preferably, the active agent is a member selected from the group consisting of carbidopa (alpha-methyl-L-DOPA hydrazine), benserazide (N-[DL-seryl]-N'-[2,3,4-trihydroxybenzyl]hydrazine), NSD 1015 (m-hydroxybenzylhydrazine), beta-alphahydrazino-alpha-methyl-propionic acid, or MK 485 (beta-[3,4-dihydroxyphenyl]-alphahydrazino-alpha-methyl propionic acid). In the preferred embodiment, active agents are exerted only in the peripheral nervous system. More preferably the active agent is carbidopa, benserazide or MK 485 (beta-[3,4-dihydroxyphenyl]-alphahydrazino-alpha-methyl propionic acid). Most preferably the active agent is carbidopa.

In one embodiment, the peripheral amino acid decarboxylase inhibitor is administered in an amount of at least about 0.01 mg per 100 kg body weight, preferably at least about 0.1 mg per 100 kg body weight, and more preferably at least about 1 mg per 100 kg body weight. The peripheral amino acid decarboxylase inhibitor is generally administered in an amount of at most about 500 mg per 100 kg body weight, preferably at most about 250 mg per 100 kg body weight, and more preferably at most about 100 mg per 100 kg body weight.

In another embodiment, the method may utilize 5HT antagonists (altanserin tartrate; amesergide; ketanserin; ritanserin), 5HT inhibitors (cinanserin hydrochloride; fenclonine; fonazine mesylate; xylamidine tosylate), and 5HT receptor antagonists (tropanserin hydrochloride) as long as these compounds remain peripherally-acting agents and do not affect the central nervous system.

In another embodiment of the invention, an active agent as set forth herein is administered locally to increase lactation. In this embodiment, suitable pharmacologically active agents include, but are not limited to: peripherally-acting aromatic amino acid decarboxylase (AADC) inhibitors, peripherally-acting tryptophan hydroxylase (TPH) inhibitors, peripherally-acting serotonin (5-HT) receptor antagonists, and mixtures thereof. Some agents, as may be seen, are encompassed by more than one of the above categories.

The active agent may be administered in the form of a pharmaceutically acceptable salt, ester, amide or prodrug or combination thereof. However, conversion of inactive ester, amide or prodrug forms to an active form must occur prior to or upon reaching the target tissue or cell. Salts, esters, amides and prodrugs of the active agents may be prepared using standard procedures known to those skilled in the art of synthetic organic chemistry and described. For example, acid addition salts are prepared from the free base (typically wherein the neutral form of the drug has a neutral —NH2 group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on a drug are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups, which may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc. The amount of active compound administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art. Preferably, the administration of the compounds is oral.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained.

It may be desirable to deliver the active agent in a dosage form that provides for controlled or sustained release of the agent. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch.

The compounds of the invention may also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

Alternatively, the pharmaceutical compositions of the invention may be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

Nasal aerosol or inhalation may also administer the pharmaceutical compositions of the invention. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations that are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

The pharmaceutical formulation may contain one or more pharmacologically active agents in addition to the peripherally-acting aromatic amino acid decarboxylase (AADC) inhibitors, peripherally-acting tryptophan hydroxylase (TPH) inhibitors, peripherally-acting serotonin (5-HT) receptor antagonists, or mixtures thereof.

Somatotropins, cholines, estrogens, prolactin, vitamins, amino acids, long-chain fatty acids, salts, L-tryptophan, 5-hydroxy-L-tryptophan or combinations thereof are preferred additional agents.

In more general terms, one would create a combination of the present invention by choosing a dosage of first component compound according to the spirit of the above guideline, and choosing dosages of the second compound in the general range of from about 1 to about 240 mg/dose. More preferred dosages, depending on the compound, would be from about 1 to about 100 mg/dose, and even more preferred dosages would be likely to be found in the range of from about 1 to about 50 mg/dose, ideally from about 1 to about 25 mg/dose. Similarly, one would choose a dose of the third component in the above range, more preferably in a range from about 10 to about 1000 mg/day, but always in a range chosen with regard to the effects of the first and second components.

The therapy of the present invention is carried out by administering a first component together with one each of the second and third component compounds in any manner that provides effective levels of the compounds in the body at the same time. All of the compounds concerned are orally available and are normally administered orally, and so oral administration of the adjunctive combination is preferred. They may be administered together, in a single dosage form, or may be administered separately.

The amount of active agent administered, and the dosing regimen used, will, of course, be dependent on the particular drug selected, the age and general condition of the subject being treated, the level of effect required. Generally, the daily dosage when administered locally will be less than the dosage normally given in conjunction with systemic modes of administration. Alternatively, a large initial loading dose can be used to achieve effective levels of the agent and can be followed by smaller doses to maintain those levels. A typical daily dose of an active agent as administered locally is generally in the range of approximately 0.1 to 500 mg. Preferably, a daily dose of an active agent as administered locally is generally in the range of approximately 1 to 250 mg. Depending on the half-life of the drug and the availability via the chosen route of administration, the dosing regimen can be modulated in order to achieve satisfactory increase of lactation.

Dosages may be adjusted appropriately to achieve desired drug levels, locally or systemically. In the event that the response in a subject is insufficient at the above doses, even higher doses (or effective higher doses by a different, more localized delivery route) may be employed to the extent that subject tolerance permits.

EXAMPLES

By suppression subtractive hybridization cloning (Diatchenko, L. et al. Suppression subtractive hybridization: a method for generating differentially regulated or tissue-specific cDNA probes and libraries. *Proc Natl Acad Sci USA* 93, 6025-6030. (1996)), we identified genes that were differentially expressed in mammary gland tissues from PRL-deficient (PRL−/−) mice (Horseman, N. D. et al. Defective mammopoiesis, but normal hematopoiesis, in mice with a targeted disruption of the prolactin gene. *EMBO J* 16, 6926-6935 (1997)) compared with mice made hyperprolactinemic by pituitary grafting (18 days), or with mice that were treated by implanting progesterone-containing pellets (25 mg, 18 days). Of the several genes identified as being PRL-dependent, 8 of an initial 25 clones that we sequenced encoded cDNA fragments for tryptophan hydroxylase (EC1.14.16.4, TPH) which catalyzes the first step in the conversion of tryptophan to serotonin (5-hydroxytryptamine, 5-HT). The sequence of the mammary-derived TPH cDNA was identical to that of the mouse TPH gene reported from a mastocytoma except for a 1 base difference in the 5'-untranslated region (Genbank accession number: AF273257).

We were able to confirm the induction of TPH by PRL using several additional lines of evidence. First, we performed differential hybridization to arrayed mouse cDNAs (Clontech Mouse Atlas version 1.2, Palo Alto, Calif.) and observed that TPH mRNA was induced in the mammary glands of mice treated with PRL, and that the TPH signal intensity in PRL-stimulated mammary glands was among the upper 10% of 1200 genes. Secondly, we observed that there were two TPH transcripts (1.8 and 3.8 kilobases) in mouse mammary gland extracts, as has been shown in other 5-HT-producing non-neuronal tissues (Stoll, J. & Goldman, D. Isolation and structural characterization of the murine tryptophan hydroxylase gene. *J Neurosci Res* 28, 457-465. (1991)). We went on to perform quantitative real-time RT-PCR (Kang, J. J. et al. Transcript quantitation in total yeast cellular RNA using kinetic PCR. *Nucleic Acids Res* 28, e2. (2000)), and observed that the absolute level of TPH mRNA in the mouse mammary gland was dramatically induced by pituitary grafting (556±29 vs. 14.4±3.8 fmol·µg$^{-1}$ of total RNA, mean±s.e.m.). In addition to the mouse mammary gland the TPH gene was expressed in normal human breast (total RNA, Stratagene, Inc., La Jolla, Calif.), and in both non-transformed human breast epithelial cells (MCF10A cells) and T47D human breast cancer cells (not shown).

Having confirmed that the TPH gene is regulated in the mammary gland, we wanted to determine whether the mouse mammary gland can synthesize either of the major bioactive indoleamines (i.e., 5-HT or melatonin). To this end, we first assessed the expression of specific genes that are important for indoleamine biosythesis. TPH converts L-tryptophan to 5-hydroxy-L-tryptophan (5-HTP), which is metabolized to 5-HT by aromatic amino acid decarboxylase (AADC, EC4.1.1.28). AADC was constitutively expressed in mouse mammary glands, and modestly induced by pituitary grafting, in contrast with TPH expression, which was highly dependent on PRL (FIG. 1*a*). Melatonin is the other major bioactive indoleamine, and the enzyme that is necessary to convert 5-HT to melatonin (serotonin N-acetyltransferase, SNAT) was not detected in the mammary gland. Therefore, we infer that the mammary gland may synthesize and secrete 5-HT, but not melatonin; and, that agents that affect that activity of TPH or AADC may alter mammary gland function. Using in situ hybridization (FIG. 1*b*-*c*) and immunohistochemistry (FIG. 1*d*-*e*) we observed that TPH mRNA, and 5-HT, respectively, were localized in the epithelial cells of the mouse mammary gland.

Figure 2:
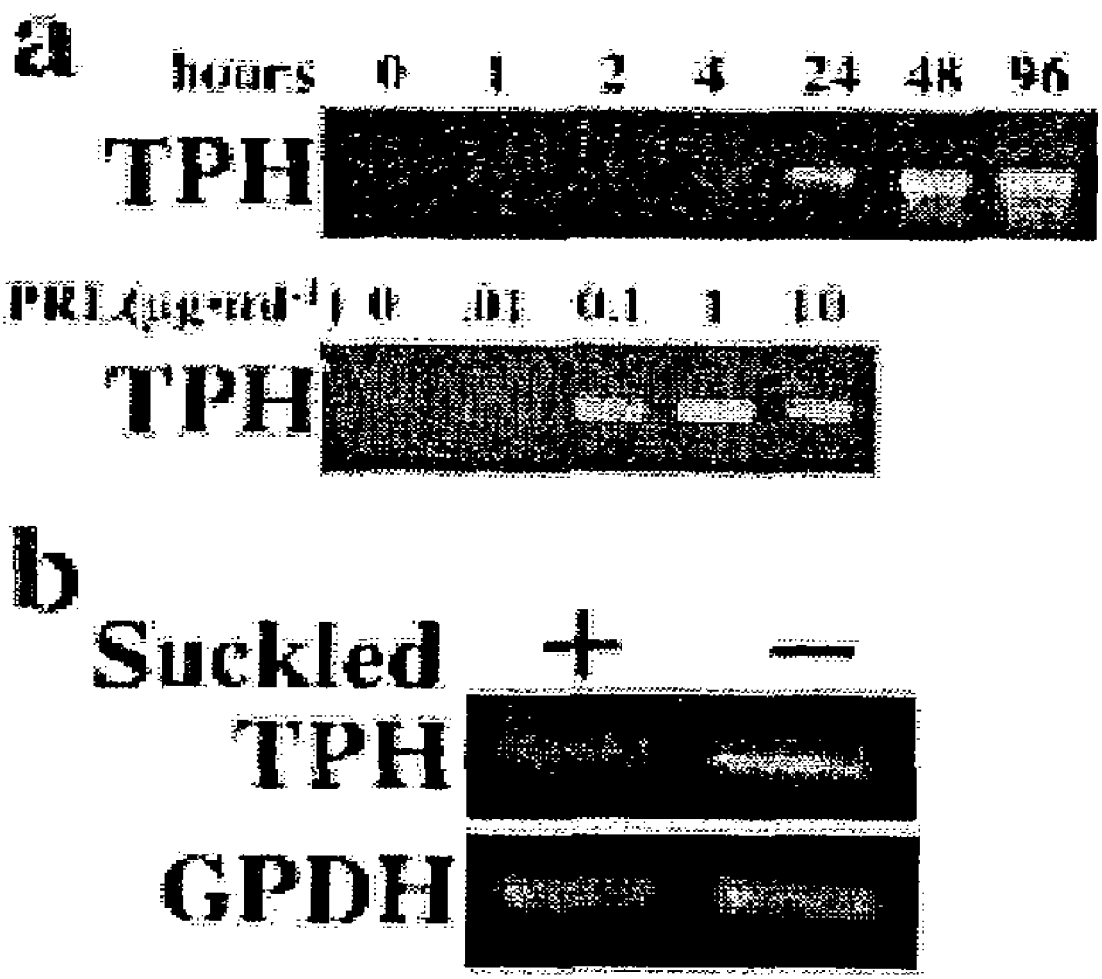
FIG. 2 shows: (a) Time-course and dose-response profile of TPH mRNA induction in primary mouse mammary epithelial organoids. (b) TPH induction by milk stasis. Contralateral #3 glands were either open and suckled (+) or sealed with cyanoacrylate glue and unsuckled (−). RT-PCR was performed for TPH and glyceraldehyde-phosphate-dehydrogenase (GPDH), as shown.

Having established that mammary gland TPH expression was induced in vivo we studied TPH induction in primary cultures of mammary epithelial organoids. These organoids, sometimes referred to as "mammospheres," secrete milk proteins, fluids and ions vectorially into a closed central lumen when cultured with lactogenic hormones. TPH increased slowly for at least 48 h following addition of PRL to the medium, and the optimum PRL dose was 1 µg/ml (approximately 20 nM) (FIG. 2*a*). While these experiments showed that PRL was important, three lines of evidence suggested that TPH induction was secondary to other synthesis and secretory processes that are stimulated by PRL. First, the time course of TPH mRNA induction was much slower that other genes known to be directly regulated by PRL. Secondly, the in vitro induction was blocked by cycloheximide; and thirdly, the TPH promoter was not induced by PRL in reporter gene assays (unpublished results).

Having established that PRL plays an important, but probably indirect, role in regulating TPH expression, we chose to investigate whether lactation, per se, is important. We were able to take advantage of a well-established experimental approach wherein the nipples of selected glands are sealed in nursing dams, while pups are allowed to continue normal suckling of the remaining unsealed glands. Using this approach both the suckled and unsuckled glands are exposed to the same extrinsic hormonal milieu, but to different intrinsic signals because of milk stasis in the unsuckled glands. FIG. 2*b* shows typical results of TPH gene expression in the #3 mammary glands of a dam where one side was left open to be suckled, and the other was sealed so that it was unsuckled. While TPH was expressed in both glands, the average TPH level was approximately 2-fold greater in the contralateral unsuckled glands (densitometric scans, n=6, P<0.05, paired T-test). We conclude that TPH gene expression is induced by milk stasis. Consequently, TPH expression and 5-HT synthesis can be dynamically modulated during the cycle of emptying and filling of the glands.

In sum, our in vivo and vitro experiments demonstrated that the mammary epithelium has the capacity to synthesize 5-HT, and this process is highly dependent on the extrinsic hormonal milieu, and milk stasis within the glands. Once we had established that 5-HT is tightly regulated in the mammary glands we went on to ask whether mammary-derived 5-HT might have an important role in the regulation of mammary gland function. Our first goal was to determine whether receptors for 5-HT are expressed in the epithelium and/or stroma of the mammary gland.

Figure 3:
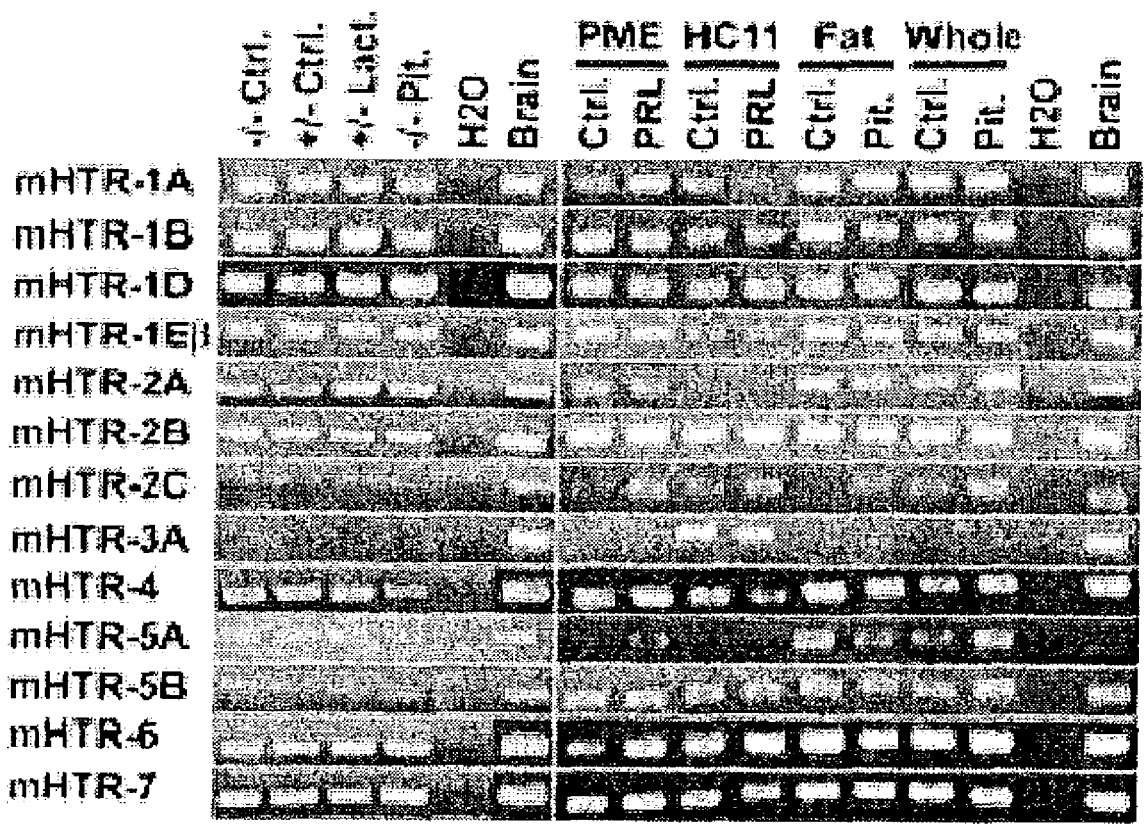
FIG. 3 shows an expression profile for mouse 5-HT receptor (mHTR) mRNA in mammary-derived extracts. Primers specific to each of the 13 subtypes of mHTR designated at the left margin were used to amplify cDNAs. The sources of mRNA include PRL gene disrupted mammary glands (−/−), and normal heterozygotes (+/−) that were either nulliparous controls (Ctrl.) or lactating (Lact.), or pituitary-grafted (Pit.). Negative controls (no added RNA, H2O) and positive controls (Brain extract) were included for each product. Primary mouse mammary epithelia (PME), HC11 cells, cleared mammary fat pad (Fat) and intact glands (Whole) were either untreated or stimulated.

We examined by RT-PCR the expression of 13 different 5-HT receptor (HTR) subtypes in mammary tissues and cells representing various states of development (FIG. 3). Twelve of the subtypes of HTR were observed both in vivo and in vitro in normal mammary gland cells. There were no robust changes in expression levels under different hormonal conditions. Type 2C receptor expression was low and variable, but without any consistent pattern in the replicate experiments. Interestingly, the HC11 clonal mouse epithelial cell line was the only cell type that expressed HTR-3A; but these cells did not express HTR-2A or 5A, suggesting the possibility that HTR signaling may have been altered by selection during establishment of these cells. Although these data address expression of HTR genes only at the mRNA level, they suggest that mammary gland cells have not only the capacity to synthesize 5-HT, but also the ability to respond to 5-HT in an autocrine/paracrine fashion.

Figure 4:
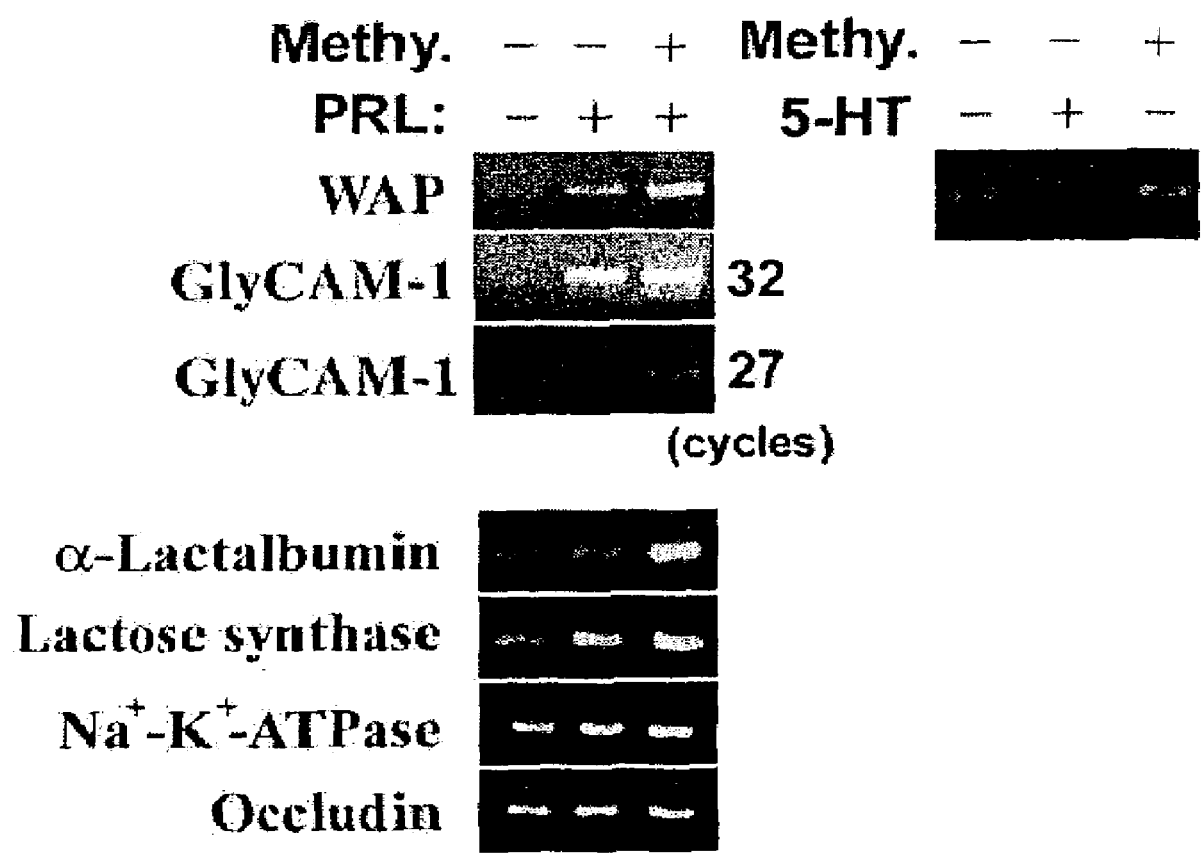
FIG. 4 shows the alteration of mammary gene expression by serotonergic agents. Primary mouse mammary cultures were treated with PRL, methysergide (Methy.), or 5-HT as noted (+). RT-PCR products for various genes expressed in the mammary gland are shown by the labels at the left margin.
Figure 5:
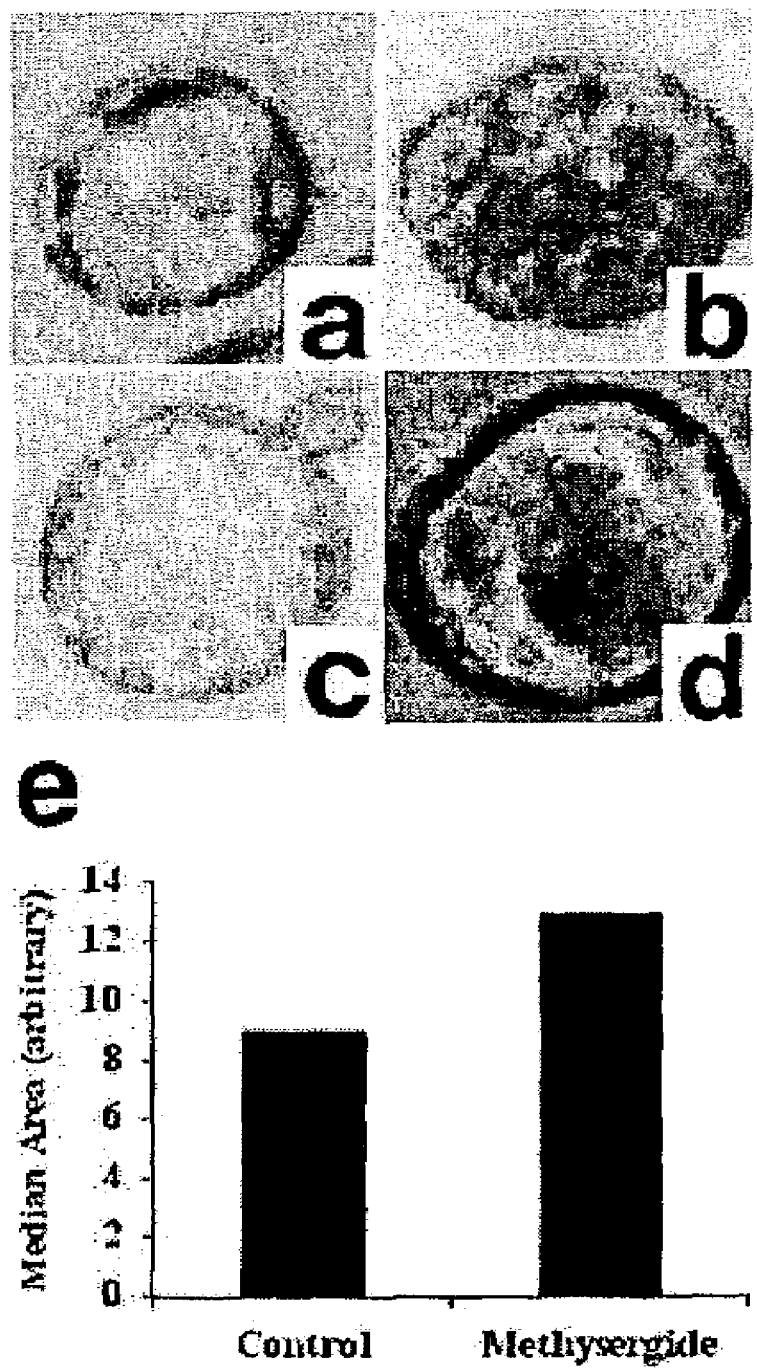
FIG. 5 shows the effects of serotonergic agents on cultured mammospheres. Qualitative comparison of typical mammospheres in cultures treated with (a) control; (b) 5-HT; (c) methysergide; (d) PCPA. Each of the agents was added to the medium at a concentration of 1 µg·ml$^{-1}$ and replenished each day during a 7-day incubation. (e) histogram depicting the median areas (in arbitrary units) of mammospheres sorted by size (n=350, 2 replicate experiments) of control- and methysergide-treated cultures.

We tested whether 5-HT might have an autocrine/paracrine effect first by examining the expression of various genes in mammosphere cultures (FIG. 4), and then by morphometry (FIG. 5). Using a broad-spectrum 5-HT receptor antagonist methysergide, in combination with PRL, we observed that the expression levels of several mammary gland genes, including whey acidic protein (WAP), glycosylated cell adhesion molecule-1 (GlyCAM-1) and α-lactalbumin. The effects of both 5-HT and methysergide (agonist and antagonist) were tested using cells cultured in 1% fetal serum, wherein the WAP gene is constitutively expressed at a low level. Under these conditions 5-HT suppressed WAP, and methysergide induced WAP. We infer from these results that 5-HT restrains milk protein gene expression in cultured mammospheres, and that relieving the cells from the 5-HT signal permits higher levels of milk protein gene expression.

In addition to the effects on gene expression shown above, perturbing 5-HT signaling caused morphological changes in mammosphere cultures. Under control conditions the mammospheres were comprised of a boundary layer surrounding an interior lumenal space (FIG. 5a). Qualitatively, mammospheres treated with different serotonergic agents had markedly different structures. Treatment with either of two anti-serotonergic agents, methysergide or the TPH inhibitor p-chloro-phenylalanine (PCPA), resulted in mammospheres that had easily visible central lumena (FIGS. 5a, 5c, 5d). Those treated with PCPA were very distinctive because the boundary layer was consistently thin, and, there was a very high contrast between the dark boundary and light central space. Conversely, those treated with 5-HT (FIG. 5b) appeared to be either filled or collapsed, with no obvious lumen.

We performed a morphometric comparison of control and methysergide-treated mammospheres employing a Macintosh computer using the public domain NIH Image program (developed at the U.S. National Institutes of Health and available on the Internet at http://rsb.info.nih.gov/nih-image/). Threshold was adjusted to automatically outline the mammospheres, and the organoids were sorted into a frequency distribution based on particle sizes. The median size of the methysergide-treated mammospheres was about 40% larger than the control mammospheres (p<0.01; Mann-Whitney U-test; FIG. 5e). In cultures treated with 5-HT the mammospheres appeared to be smaller than the controls, but because they were qualitatively different in appearance a quantitative morphometric comparison was not appropriate.

Our observations that blockade of 5-HT signaling in vitro stimulated milk protein synthesis (FIG. 4) and mammosphere dilation (FIG. 5) had potentially important implications for the physiological regulation of milk yield in vivo. We reasoned that milk yield might increase if 5-HT signaling in the mammary gland were interrupted, but testing this idea was complicated by the fact that 5-HT in the central nervous system regulates PRL secretion, and many potentially useful pharmacological agents influence central 5-HT functions. For this reason we chose to use the peripherally-acting AADC inhibitor carbidopa (S-(−)-α-hydrazino-3,4-dihydroxy-2-methylbenzenepropanoic acid) to test the idea that suppressing 5-HT synthesis in peripheral tissues, including the mammary gland, would alter milk secretion in mice.

Nursing dams were given 4 injections of carbidopa (1 mg/kg body weight) at 12 h intervals (or control vehicle). After the final injection the pups were removed from the dam for 4 h. At the end of 4 h the dams were weighed and reunited with the pups to nurse for 1 h. After the nursing interval the dams were again weighed and the nursing-related weight losses were analyzed as an index of milk yield (Table 1).

TABLE 1

Carbidopa increases milk yield.

| Treatment | Dam Body Weight | Milk Yield | Litter Weight | Litter/Dam |
|---|---|---|---|---|
| Vehicle(8) | 38.2 ± 1.1 | 1.8 ± 0.1 | 32.7 ± 0.9 | 0.86 ± 0.02 |
| Carbidopa(9) | 39.6 ± 1.2$^{ns}$ | 2.1 ± 0.1* >16.7% | 36.5 ± 1.8* >11.6% | 0.93 ± 0.03* >8.1% |

The litters of lactating dams (mice) were adjusted to 8 pups on day 1 postpartum. Carbidopa (1 mg/kg in 45% hydroxypropyl-β-cyclodextrin) or control vehicle were injected at approximately 12 h intervals beginning in the evening of postpartum day 3. After 4 injections (morning of day 5) pups were separated from the dams for 4 h. At the end of separation interval, the dams were injected with oxytocin (0.2U) and both the dams and their litters and were weighed. The litters were reunited with the dams for a 1 h nursing interval. The weights of the dams were measured after nursing and the differences in the weights of the dams before and after nursing are reported as milk yield. The percent increases with carbidopa-treatment are shown for statistically significant variables.

Weight values expressed in grams (g) as means±s.e.m; ns: not significantly different; *: $p \leq 0.05$ by parametric and nonparametric T-tests. Numbers of animals in treatment groups are in parentheses.

Carbidopa-treated dams had a 16.7% greater milk yield than did their control counterparts. The weights of the pups in the carbidopa-treated litters were 10.9% greater than the controls on an absolute basis, and 6.4% greater when expressed relative to the mothers' weights. This indicates that blocking peripheral AADC activity for two days resulted in a sustained increase in milk yield to the pups. Thus, the in vivo results are consistent with the in vitro findings, and support the conclusion that 5-HT acts as an autocrine inhibitor of lactation.

Milk stasis results in both the rapid down-regulation of milk synthesis and secretion, and, if sustained, to involution of the gland. During the first phase of involution lobuloalveolar cells begin to undergo apoptosis. After 3-5 days the involution process enters its second phase, wherein a wholesale remodeling of the mammary gland leads to regression of the epithelium and reestablishment of the adipose stroma. Several of the local factors that mediate involution after weaning have been identified.

Methods

Prolactin-deficient mice, made congenic on C57BL6/J by 8 backcross generations, were made hyperprolactinaemic by grafting a normal anterior pituitary gland under the kidney capsule, or were treated with a progesterone tablet (25 mg) implanted subcutaneously for 18 days, or they were sham-operated. Progesterone-treated mammary tissue served as a control for the subtractive cloning to eliminate genes indirectly regulated by PRL via its stimulatory effect on the ovary. The mice were maintained on an L,D: 14,10 daily light, darkness cycle with food and water available ad libitum. All experiments were conducted under IACUC-approved protocols. The cDNAs specifically expressed in the PRL-stimulated breast were cloned by suppression subtractive hybridization using reagents and protocols from CLONTECH Laboratories, Inc. (Palo Alto, Calif.).

Localization of TPH mRNA by in situ hybridization in mammary gland tissue sections was performed as described (Hou, Z. et al. Glycosylation-dependent cell adhesion molecule 1 (GlyCAM 1) is induced by prolactin and suppressed by progesterone in mammary epithelium. *Endocrinology* 141, 4278-4283. (2000)). Immunohistochemical detection of 5-HT was performed on 5-μm paraffin-embedded sections using a monoclonal anti-5-HT (H209, Dako, Corp., Carpinteria, Calif.), which was visualized by a Cy3-conjugated streptavidin-biotin secondary antibody system (Histomouse SP, Zymed, Corp., South San Francisco, Calif.).

Primary mouse mammary epithelium was prepared from nulliparous mice by enzymatic digestion and differential trypsinization, modifying the method of Imagawa (Pedchenko, V. K. & Imagawa, W. T. Mammogenic hormones differentially modulate keratinocyte growth factor (KGF)-induced proliferation and KGF receptor expression in cultured mouse mammary gland epithelium. *Endocrinology* 139,2519-2526 (1998)). Enriched epithelial cells ($2\times10^5$ cells per well) were plated in basement membrane (Matrigel, 0.5 ml/well, BD Biosciences) reconstituted in a 12-well plate so that they formed mammospheres. They were pre-incubated for seven days, and treated with ovine PRL (1 μg/ml) for 2 days. The cell culture experiments were replicated 2-3 times in all cases.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patents, patent applications, and publications mentioned herein are hereby incorporated by reference.

The invention claimed is:

1. A method of treatment for enhancing lactation in a mammal comprising
   a) identifying a subject mammal in need of such treatment
   b) administering to the subject mammal in need of such treatment an effective amount of a pharmacologically active agent capable of inhibition of serotonin action in mammary glands and enhancing lactation in the subject mammal;
   wherein the active agent is one or more inhibitor of aromatic L-amino acid decarboxylase selected from the group consisting of carbidopa, benserazide, NSD 1015, beta-alphahydrazino-alpha-methyl-propionic acid, MK 485 and mixtures thereof.

2. The method of claim 1 wherein the active agent is administered in a predetermined dosing regimen.

3. The method of claim 1, wherein the active agent is used in conjunction with at least one additional pharmacologically active agent, together with a pharmaceutically acceptable carrier.

4. The method of claim 3, wherein the additional pharmacologically active agent is a serotonin receptor antagonist.

5. The method of claim 4, wherein the serotonin receptor antagonist is selected from the group consisting of ketanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, granisetron, LSD, 2-bromo-CSD (BOL), xylamidine, 1-(–)-cocaine, and mixtures thereof.

6. The method of claim 1 wherein the active agent is an inhibitor of L-aromatic amino acid decarboxylase and is administered in an amount between about 5 and about 75 milligrams per day.

7. The method of claim 6, wherein the administration of the pharmacologically active agent is by a delivery method selected from the group consisting of oral, parenteral, buccal, rectal, topical, transdermal and a combination thereof.

8. The method of claim 2, wherein the pharmacologically active agent is used in conjunction with at least one additional pharmacologically active agent, together with a pharmaceutically acceptable carrier.

9. The method of claim 8, wherein the additional pharmacologically active agent is a serotonin receptor antagonist.

10. The method of claim 9, wherein the serotonin receptor antagonist is selected from the group consisting of ketanserin, cinanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxylate methiodide, methysergide, risperidone, cyproheptadine, clozapine, mianserin, ritanserin, granisetron, LSD, 2-bromo-CSD (BOL), xylamidine, 1-(–)-cocaine, and mixtures thereof.

11. The method of claim 10, wherein the serotonin receptor antagonist exerts an effect only in the peripheral nervous system.

12. The method of claim 11, wherein the serotonin receptor antagonist is administered in an amount of at least about 0.1 mg per 100 kg body weight.

13. The method of claim 11, wherein the serotonin receptor antagonist is administered in an amount of at most about 250 mg per 100 kg body weight.

14. The method of claim 1, wherein the administration of the amino acid decarboxylase inhibitor is oral.

15. The method of claim 8, wherein the additional agent is selected from the group consisting of lactational enhancers, somatotropins, cholines, estrogens, prolactin, vitamins, amino acids, long-chain fatty acids, salts, L-tryptophan, 5-hydroxy-L-tryptophan and combinations thereof.

16. The method of claim 1, wherein the inhibitor of aromatic L-amino acid decarboxylase is one or more agents selected from the group consisting of carbidopa, benserazide or MK 485 and mixtures thereof.

17. The method of claim 1, wherein the inhibitor of aromatic L-amino acid decarboxylase is one or more agents selected from the group consisting of carbidopa, benserazide and mixtures thereof.

18. The method of claim 1, wherein the inhibitor of aromatic L-amino acid decarboxylase is carbidopa.

19. The method of claim 18, wherein the amino acid decarboxylase inhibitor is administered in an amount of at least about 0.1 mg per 100 kg body weight.

20. The method of claim 18, wherein the amino acid decarboxylase inhibitor is administered in an amount of at most about 250 mg per 100 kg body weight.

21. The method of claim 3, wherein the additional agent is selected from the group consisting of lactational enhancers, somatotropins, cholines, estrogens, prolactin, vitamins, amino acids, long-chain fatty acids, salts, L-tryptophan, 5-hydroxy-L-tryptophan and combinations thereof.

22. The method of claim 21, wherein the additional agent is a lactational enhancer selected from the group consisting of 11,17-dimethoxy-18-((3,4,5-trimethoxybenzoyl)oxy)yohimban-16-carboxylic acid methyl ester, 4-amino-5-chloro-N-((2-diethylamino)ethyl)-2-methoxybenzamide, and combinations thereof.

* * * * *